United States Patent
Venugopala et al.

(10) Patent No.: US 11,970,470 B1
(45) Date of Patent: Apr. 30, 2024

(54) {5-CHLORO-2-(2-(3-(SUBSTITUTEDPHENYL)-1,2,4-OXADIAZOL-5-YL)ETHYL)PHENYL} (PHENYL)METHANONES AS LARVICIDAL AGENTS

(71) Applicant: KING FAISAL UNIVERSITY, Al-Ahsa (SA)

(72) Inventors: Katharigatta N. Venugopala, Al-Ahsa (SA); Pran Kishore Deb, Ranchi (IN); Rashmi Venugopala, Durban (ZA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/388,728

(22) Filed: Nov. 10, 2023

(51) Int. Cl.
*A01P 7/04* (2006.01)
*A01N 43/82* (2006.01)
*C07D 271/06* (2006.01)

(52) U.S. Cl.
CPC .......... *C07D 271/06* (2013.01); *A01N 43/82* (2013.01); *A01P 7/04* (2021.08)

(58) Field of Classification Search
CPC combination set(s) only.
See application file for complete search history.

(56) References Cited

PUBLICATIONS

National Center for Biotechnology Information (2023). PubChem Compound Summary for CID 46702264, [5-Chloro-2-[[3-(2,5-difluoro-4-methylphenyl)-1,2,4-oxadiazol-5-yl]methoxy]phenyl]-phenylmethanone. Retrieved Nov. 9, 2023 from https://pubchem.ncbi.nlm.nih.gov/compound/46702264.

PubChem first 10 most relevant similar to known example 5d, Retrieved Nov. 9, 2023 from https://pubchem.ncbi.nlm.nih.gov/#query=C1%3DC(C(%3DCC(%3DC1C2%3DNOC(%3DN2)COC3%3DCC%3DC(C%3DC3C(C4%3DCC%3DCC%3DC4)%3DO)CI)%5BF%5D)C)%5BF%5D&tab=similarity.

Neithnadka Premsai Rai, et al.; "Design, synthesis, characterization, and antibacterial activity of {5-chloro-2-[(3-substitutedphenyl-1,2,4-oxadiazol-5-yl)-methoxy]-phenyl}-(phenyl)-methanones"; European Journal of Medicinal Chemistry vol. 45, Issue 6, Jun. 2010, pp. 2677-2682.

P. Subbaraj, et al.; "Mixed Ligand Complexes Containing (2-Hydroxy-4-Methoxyphenyl) (Phenyl) Methanone and 2-Aminophenol: Synthesis and DNA Cleavage"; International Journal of Emerging Science and Engineering (IJESE) ISSN: 2319-6378, vol. 1, Issue-7, May 2013.

Katharigatta Narayanaswamy Venugopala, et al.; "1,2,3-Triazolyltetrahydropyrimidine Conjugates as Potential Sterol Carrier Protein-2 Inhibitors: Larvicidal Activity against the Malaria Vector Anopheles arabiensis and In Silico Molecular Docking Study"; Apr. 2022Molecules 27(9):2676 DOI:10.3390/molecules27092676; License CC BY 4.0.

*Primary Examiner* — Alicia L Otton
(74) *Attorney, Agent, or Firm* — Nath, Goldberg & Meyer; Richard C. Litman

(57) ABSTRACT

Compounds for treating preventing malaria and, particularly, to larvicidal agents that are {5-chloro-2-(2-(3-(substitutedphenyl)-1,2,4-oxadiazol-5-yl)ethyl)phenyl}(phenyl) methanones derivatives and their use as larvicidal agents.

18 Claims, No Drawings

{5-CHLORO-2-(2-(3-(SUBSTITUTEDPHENYL)-1,2,4-OXADIAZOL-5-YL)ETHYL)PHENYL}(PHENYL)METHANONES AS LARVICIDAL AGENTS

BACKGROUND

1. Field

The present disclosure relates to synthesis of {5-chloro-2-(2-(3-(substitutedphenyl)-1,2,4-oxadiazol-5-yl)ethyl)phenyl}(phenyl)methanones as larvicidal agents and their use as larvicidal agents.

2. Description of the Related Art

Malaria is considered one of the most challenging life-threatening diseases initiated by parasites that are transmitted to humans through the bites of infected *Anopheles* mosquitoes. It affects both genders, leading to severe health impacts and negative socioeconomic impacts. Recently, the World Health Organization (WHO) reported that there were an estimated 228 million cases of malaria spanning 87 countries. The *Anopheles arabiensis* mosquito is considered one of the major vectors of malaria. The path of infection starts with a bite from an infected female mosquito, where the parasite is delivered into circulatory system and ultimately to the liver where it become mature and reproduces.

There are many approaches and strategies for the management of Malaria. One of the most effective strategies is to eliminate the vector through environmental modifications and biological control, The use of long-lasting insecticidal nets (LLINs) and indoor residual spraying (IRS) or safe synthetic larvicidal agents are candidates for biological control. Since insecticide resistance threatens the management of vectors, it is necessary to prioritize development of potent new biological active compounds as well as to aid in resistance management.

Thus, new insecticides and/or pesticides solving the aforementioned problems are desired.

SUMMARY

In the process of designing and developing a novel larvicidal agent, a series of (5-chloro-2-(2-(3-(substitutedphenyl)-1,2,4-oxadiazol-5-yl)ethyl)phenyl)(phenyl)methanones derivatives have been developed by a three-step synthetic chemical method. The present subject matter relates to the synthesis of an anti-malarial drug designed to kill, for example, the mosquito vector *Anopheles arabiensis* at the larval stage. The compounds were evaluated for larvicidal activity, for example against *Anopheles arabiensis*, by standard WHO larvicidal protocols. Tested compounds resulted in high overall larval mortality of greater than 75% after 24 hours and 48 hours.

In an embodiment, the present subject matter relates to a compound having the formula I:

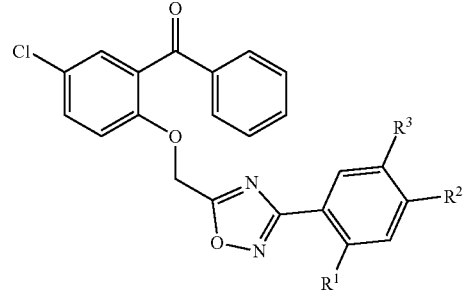

wherein:
$R^1$ is selected from the group consisting of H and F;
$R^2$ is selected from the group consisting of H, F, I, ethoxy, isopropyl, and methyl; and
$R^3$ is selected from the group consisting of H, F, Cl, methyl, and methoxy.

In a further embodiment, the present subject matter relates to a compound selected from the group consisting of: {5-chloro-2-[(3-(phenyl)-1,2,4-oxadiazol-5-yl)-methoxy]-phenyl}-(phenyl)-methanone (5a); {5-chloro-2-[(3-(4-fluorophenyl)-1,2,4-oxadiazol-5-yl)-methoxy]-phenyl}-(phenyl)-methanone (5b); {5-chloro-2-[(3-(4-iodophenyl)-1,2,4-oxadiazol-5-yl)-methoxy]-phenyl}-(phenyl)-methanone (5c); {5-chloro-2-[(3-(2,5-difluoro-4-methylphenyl)-1,2,4-oxadiazol-5-yl)-methoxy]-phenyl}-(phenyl)-methanone (5d); {5-chloro-2-[(3-(4-ethoxyphenyl)-1,2,4-oxadiazol-5-yl)-methoxy]-phenyl}-(phenyl)-methanone (5e); {5-chloro-2-[(3-(3-chloro-4-fluorophenyl)-1,2,4-oxadiazol-5-yl)-methoxy]-phenyl}-(phenyl)-methanone (5f); {5-chloro-2-[(3-(4-isopropylphenyl)-1,2,4-oxadiazol-5-yl)-methoxy]-phenyl}-(phenyl)-methanone (5g); {5-chloro-2-[(3-(4-fluoro-3-methylphenyl)-1,2,4-oxadiazol-5-yl)-methoxy]-phenyl}-(phenyl)-methanone (5h); and {5-chloro-2-[(3-(4-fluoro-3-methoxyphenyl)-1,2,4-oxadiazol-5-yl)-methoxy]-phenyl}-(phenyl)-methanone (5i).

In one embodiment, the present subject matter relates to a method of killing insects and larva, the method comprising applying to the food of said insects and larva in a target site of insect infestation a larvicidal effective amount of a larvicidal active composition comprising a compound of the formula I and an acceptable carrier:

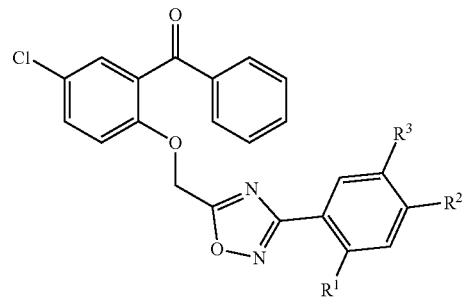

wherein:
  $R^1$ is selected from the group consisting of H and F;
  $R^2$ is selected from the group consisting of H, F, I, ethoxy, isopropyl, and methyl; and
  $R^3$ is selected from the group consisting of H, F, Cl, methyl, and methoxy.

In various embodiments, $R^1$ may be H; $R^2$ may be selected from the group consisting of H, F, I, ethoxy, isopropyl, and methyl; and $R^3$ may be selected from the group consisting of H, Cl, methyl, and methoxy. In other embodiments, $R^1$ is F, $R^2$ is methyl, and $R^3$ is F.

In another embodiment, the present subject matter relates to the use of an insecticidally acceptable composition comprising an insecticidally effective amount of the compounds of formula I, including a number of species or specific structures falling under structural formula I.

In a further embodiment, the present subject matter relates to a method of killing insects comprising applying to food of the insects or to a target site of insect infestation an insecticidally effective amount of compounds of formula I.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of an anti-malarial drug designed to kill, for example, the mosquito vector *Anopheles arabiensis* at the larval stage. The compounds were evaluated for larvicidal activity, for example against *Anopheles arabiensis*, by standard WHO larvicidal protocols. Tested compounds resulted in high overall larval mortality of greater than 75% after 24 hours and 48 hours.

In an embodiment, the present subject matter relates to a compound having the formula I:

I 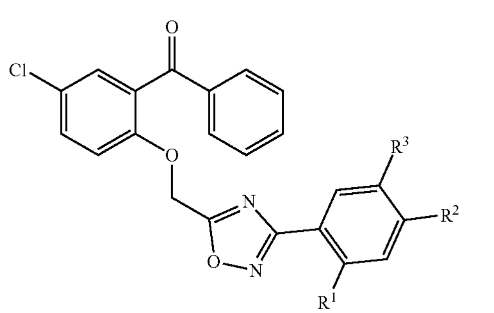 wherein:

$R^1$ is selected from the group consisting of H and F;

$R^2$ is selected from the group consisting of H, F, I, ethoxy, isopropyl, and methyl; and $R^3$ is selected from the group consisting of H, F, Cl, methyl, and methoxy.

In various embodiments, $R^1$ may be H; $R^2$ may be selected from the group consisting of H, F, I, ethoxy, isopropyl, and methyl; and $R^3$ may be selected from the group consisting of H, Cl, methyl, and methoxy. In other embodiments, $R^1$ is F, $R^2$ is methyl, and $R^3$ is F.

In certain embodiments, the compound can be selected from the group consisting of: {5-chloro-2-[(3-(phenyl)-1,2,4-oxadiazol-5-yl)-methoxy]-phenyl}-(phenyl)-methanone (5a); {5-chloro-2-[(3-(4-fluorophenyl)-1,2,4-oxadiazol-5-yl)-methoxy]-phenyl}-(phenyl)-methanone (5b); {5-chloro-2-[(3-(4-iodophenyl)-1,2,4-oxadiazol-5-yl)-methoxy]-phenyl}-(phenyl)-methanone (5c); {5-chloro-2-[(3-(2,5-difluoro-4-methylphenyl)-1,2,4-oxadiazol-5-yl)-methoxy]-phenyl}-(phenyl)-methanone (5d); {5-chloro-2-[(3-(4-ethoxyphenyl)-1,2,4-oxadiazol-5-yl)-methoxy]-phenyl}-(phenyl)-methanone (5e); {5-chloro-2-[(3-(3-chloro-4-fluorophenyl)-1,2,4-oxadiazol-5-yl)-methoxy]-phenyl}-(phenyl)-methanone (5f); {5-chloro-2-[(3-(4-isopropylphenyl)-1,2,4-oxadiazol-5-yl)-methoxy]-phenyl}-(phenyl)-methanone (5g); {5-chloro-2-[(3-(4-fluoro-3-methylphenyl)-1,2,4-oxadiazol-5-yl)-methoxy]-phenyl}-(phenyl)-methanone (5h); and {5-chloro-2-[(3-(4-fluoro-3-methoxyphenyl)-1,2,4-oxadiazol-5-yl)-methoxy]-phenyl}-(phenyl)-methanone (5i).

Said differently, the present subject matter can be related to compounds of formula I, i.e. {5-chloro-2-(2-(3-(substitutedphenyl)-1,2,4-oxadiazol-5-yl)ethyl)phenyl}(phenyl) methanones, selected from the group consisting of:

5a

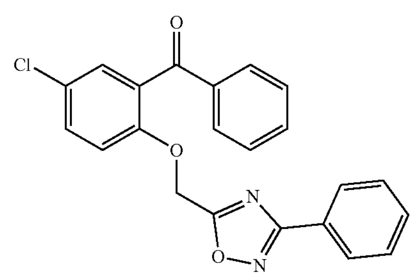

5b

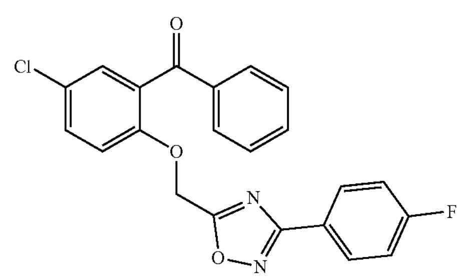

5c

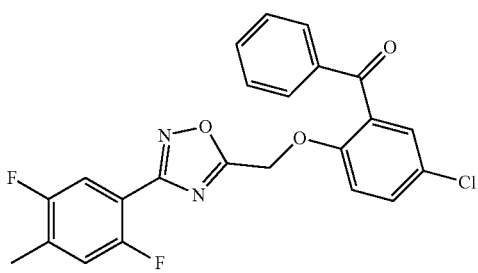

5d

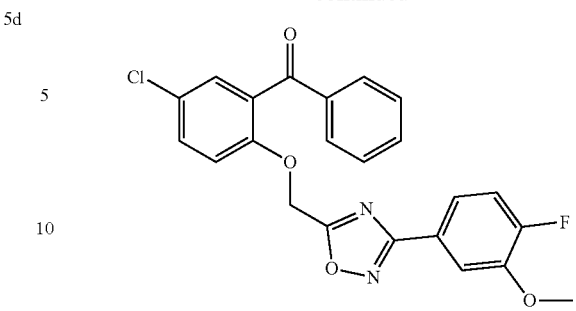

5i

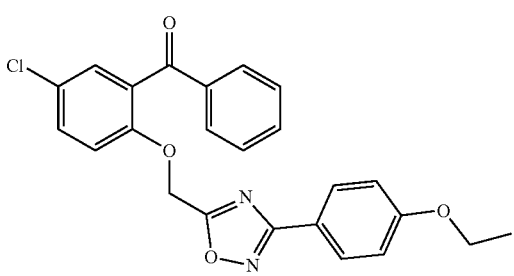

5e

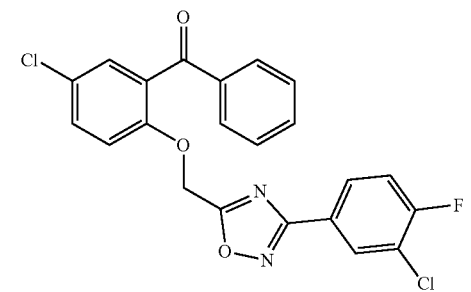

5f

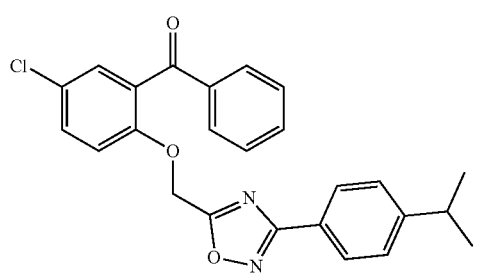

5g

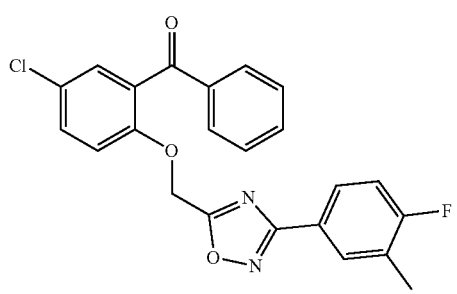

5h

It is to be understood that the present subject matter covers all combinations of substituent groups referred to herein.

In additional embodiments, the compound of formula I is considered as larvicidal agent. Accordingly, the present compound is capable of killing the larval stage of an insect.

In another embodiment, the present subject matter relates to an insecticidally acceptable composition comprising an insecticidally effective amount of compound of formula I and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While insecticidal dosage levels have yet to be optimized for the present compounds, generally, each treatment of the present compositions could be expected to include 1 mg/mL in 1 mL of a suitable carrier and 249 mL of water to obtain a final concentration of 4 µg/mL, of the present compounds. The precise effective amount will vary from treatment to treatment and will depend upon the target area of application, the insect species being treated for, the number of insects present, and the like. The treatment area may be administered in as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects and larva comprising applying to said insects or to a target site of insect infestation an insecticidally effective amount of the compound of formula I and/or a composition containing the same.

In an embodiment, the present methods of killing insects can be effective against insects belonging to a species

*Anopheles arabiensis* of mosquitos. Accordingly, the present compounds can be used as an insecticide to control populations of harmful insect pests, including, by way of non-limiting example, cockroaches and fleas.

In one embodiment, in the present methods of killing insects, the compounds as described herein can have a high larval mortality rate of 79.49±1.09 to 98.21±1.22 in 24 hours and 84.70±1.88 to 100.00±2.01 in 48 hours.

In another embodiment, in the present methods of killing insects, the compounds as described herein, as exemplified by the {5-chloro-2-[(3-(4-fluorophenyl)-1,2,4-oxadiazol-5-yl)-methoxy]-phenyl}-(phenyl)-methanone (5b) compound, can have a high larval mortality rate of 91.70±1.61 in 24 hours and 94.68±1.90 in 48 hours.

In yet another embodiment, in the present methods of killing insects, the {5-chloro-2-[(3-(3-chloro-4-fluorophenyl)-1,2,4-oxadiazol-5-yl)-methoxy]-phenyl}-(phenyl)-methanone (5f) compound can have a high larval mortality rate of 98.21±1.22 in 24 hours and 100.00±2.01 in 48 hours.

In still another embodiment, in the present methods of killing insects, the {5-chloro-2-[(3-(4-fluoro-3-methylphenyl)-1,2,4-oxadiazol-5-yl)-methoxy]-phenyl}-(phenyl)-methanone (5h) compound can have a high larval mortality rate of 83.58±2.01 in 24 hours and 86.09±1.95 in 48 hours.

In still another embodiment, in the present methods of killing insects, {5-Chloro-2-[(3-(4-fluoro-3-methoxyphenyl)-1,2,4-oxadiazol-5-yl)-methoxy]-phenyl}-(phenyl)-methanone (5i) compound can have a high larval mortality rate of 79.49±1.09 in 24 hours and 84.70±1.88 in 48 hours.

In a further embodiment of the present methods, the compounds of formula I can be applied to animal food. More specifically, the compounds of formula I can be applied to cat food. In additional embodiments, the compounds of formula I can be ingested by the larva of the species *Anopheles arabiensis*.

In an embodiment, the present methods of controlling mosquitos can be effective against mosquitos belonging to a species *Anopheles arabiensis*.

In a further embodiment, the present subject matter relates to a method of making {5-chloro-2-(2-(3-(substitutedphenyl)-1,2,4-oxadiazol-5-yl)ethyl)phenyl}(phenyl)methanones derivatives of compound I. The method begins with adding a solution of substituted benzonitriles 1 in ethanol to a solution of hydroxylamine hydrochloride and sodium carbonate in water. The reaction mixture may be heated at reflux temperature for at least about 8 hours. The reaction mixture is then cooled, and the solvent may be removed in vacuum and extracted with ethyl acetate. The combined ethyl acetate layer may be washed with water, brine, and then dried over sodium sulfate and concentrated to obtain a solid which was recrystallized using aqueous ethanol.

Next, diisopropylethylamine (DIEA) is added to a solution of N'-hydroxy substituted benzimidamides (2a-i) in dichloroethane which may then be followed by the drop wise addition of chloroacetylchloride at 0° C. The reaction mixture may be stirred for 4 hours at room temperature and then heated under reflux conditions overnight for at least about 18 hours. The reaction mixture may then be concentrated and diluted with ethyl acetate, washed with water, brine, and dried over sodium sulfate. The solution is then concentrated to dryness and purified by flash column chromatography using ethyl acetate and petroleum ether as eluent.

Finally, the method concludes with heating a mixture of 5-(chloromethyl)-3-(substitutedphenyl)-1,2,4-oxadiazole, 2-hydroxy-5-chloro-benzophenone, dried acetone, and ultra-dried potassium carbonate under reflux for at least about 8 hours. The mixture may then be cooled to room temperature and filtered. The filtrate may then be evaporated to dryness and the residue obtained may be purified by silica gel flash column chromatography with ethyl acetate:n-hexane as eluent. The present production methods can be further seen by referring to the following Scheme 1:

Scheme 1

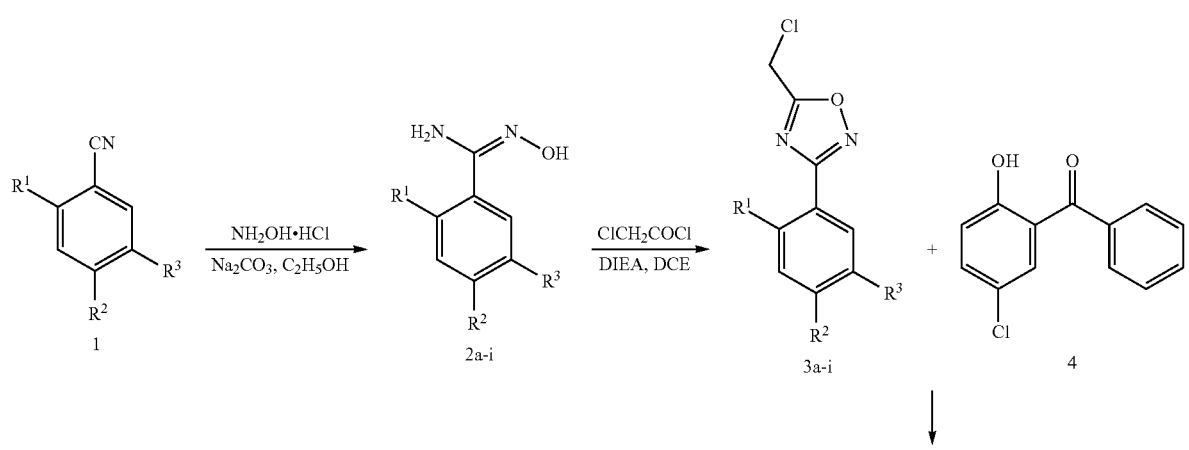

-continued

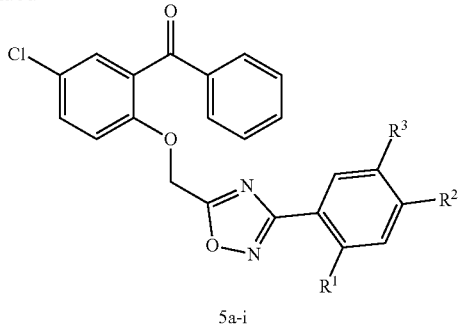

5a-i

The following examples relate to various methods of manufacturing certain specific compounds and application results as described herein. All compound numbers expressed herein are with reference to the synthetic pathway figures shown above.

EXAMPLES

The general process for designing of {5-chloro-2-(2-(3-(substitutedphenyl)-1,2,4-oxadiazol-5-yl)ethyl)phenyl}(phenyl)methanones derivatives on a three step reaction:

Example 1

General Procedure for the Preparation of N'-hydroxy Substituted benzimidamide (2a-i)

To a solution of hydroxylamine hydrochloride (0.121 mol) and sodium carbonate (0.077 mol) in water (100 mL), a solution of substituted benzonitriles 1 (0.048 mol) in ethanol (50 mL) was added. The reaction mixture was heated at reflux temperature for 8 h. After cooling the reaction mixture, the solvent was removed in vacuum and extracted with ethyl acetate. The combined ethyl acetate layer was washed with water, brine and dried over sodium sulfate and concentrated to obtain a solid which was recrystallized using aqueous ethanol.

Example 2

N'-hydroxybenzimidamide (2a)

$^1$H NMR (DMSO-d6) δ ppm: 5.82 (bs, 2H), 7.35-7.39 (m, 3H), 7.67-7.70 (m, 2H), 9.66 (bs, 1H); MS: m/z=137.1 (M$^+$).

Example 3

4-Fluoro-N-hydroxybenzimidamide (2b)

$^1$H NMR (DMSO-d6) δ ppm: 5.84 (bs, 2H), 7.19 (m, 2H), 7.68 (m, 2H), 9.63 (s, 1H); MS: m/z=155.1 (M$^+$).

Example 4

N-Hydroxy-4-iodobenzimidamide (2c)

$^1$H NMR (DMSO-d6) δ ppm: 5.84 (bs, 2H), 7.45 (d, 2H), 7.73 (d, 2H), 9.72 (s, 1H); MS: m/z=263.0 (M$^+$).

Example 5

2,5-Difluoro-N-hydroxy-4-methylbenzimidamide (2d)

$^1$H NMR (DMSO-d6) δ ppm: 2.23 (s, 3H), 5.83 (bs, 2H), 7.18-7.26 (m, 2H), 9.73 (s, 1H); MS: m/z=187.2 (M$^+$).

Example 6

4-Ethoxy-N'-hydroxybenzimidamide (2e)

$^1$H NMR (CDCl$_3$) δ ppm: 1.40-1.43 (t, 3H, CH$_3$), 4.02-4.07 (q, 2H, OCH$_2$), 4.88 (bs, 2H), 6.87-6.92 (d, 2H), 7.52-7.56 (d, 2H); MS: m/z=181.2 (M$^+$).

Example 7

3-Chloro-4-fluoro-N-hydroxybenzimidamide (2f)

$^1$H NMR (CDCl$_3$) δ ppm: 4.74 (bs, 2H), 7.24-7.29 (m, 1H), 7.97-8.00 (m, 1H), 8.16-8.18 (m, 1H); MS: m/z=189.1 (M$^+$).

Example 8

N-Hydroxy-4-isopropylbenzimidamide (2g)

$^1$H NMR (CDCl$_3$) δ ppm: 1.24-1.26 (d, 6H, 2×CH$_3$), 2.89-2.96 (q, J=6.83 Hz, 1H), 4.90 (bs, 2H), 7.24-7.26 (m, 2H), 7.54-7.56 (m, 2H); MS: m/z=179.11 (M$^+$).

Example 9

4-Fluoro-N-hydroxy-3-methylbenzimidamide (2h)

$^1$H NMR (CDCl$_3$) δ ppm: 2.31 (s, 3H, CH$_3$), 4.9 (bs, 2H), 6.99-7.03 (m, 1H), 7.39-7.47 (m, 2H); MS: m/z=169.0 (M$^+$).

Example 10

4-Fluoro-N-hydroxy-3-methoxybenzimidamide (2i)

$^1$H NMR (CDCl$_3$) δ ppm: 3.95 (s, OCH$_3$), 4.96 (bs, 2H), 7.16-7.20 (m, 1H), 7.64-7.68 (m, 2H); MS: m/z=185.16 (M$^+$).

Example 11

General Procedure for the Preparation of 5-(chloromethyl)-3-(substitutedphenyl)-1,2,4-oxadiazole (3a-i)

To a solution of N'-hydroxy substitutedbenzimidamide (2a-i) (0.0367 mol) in dichloroethane, diisopropylethylamine (DIEA) (0.0733 mol) was added followed by the drop wise addition of chloroacetylchloride (0.0367 mol) at 0° C. The reaction mixture was stirred for 4 h at room temperature, then heated under reflux conditions overnight (18 h). The reaction mixture was concentrated and diluted with ethyl acetate, washed with water, brine and dried over sodium sulfate. The solution was concentrated to dryness and purified by flash column chromatography using ethyl acetate and petroleum ether (1:9) as eluent.

Example 12

5-(Chloromethyl)-3-phenyl-1,2,4-oxadiazole (3a)

$^1$H NMR (CDCl$_3$) δ ppm: 4.76 (s, 2H), 7.48-7.54 (m, 3H), 8.08-8.11 (m, 2H); MS: m/z=195.2 (M$^+$).

Example 13

5-(Chloromethyl)-3-(4-fluorophenyl)-1,2,4-oxadiazole (3b)

$^1$H NMR (CDCl$_3$) δ ppm: 4.75 (s, 2H), 7.71-7.21 (m, 2H), 8.08-8.11 (m, 2H); MS: m/z=213.2 (M$^+$).

Example 14

5-(Chloromethyl)-3-(4-iodophenyl)-1,2,4-oxadiazole (3c)

$^1$H NMR (CDCl$_3$) δ ppm: 4.74 (s, 2H), 7.79-7.86 (m, 4H); MS: m/z=321.1 (M$^+$).

Example 15

5-(Chloromethyl)-3-(2,5-difluoro-4-methylphenyl)-1,2,4-oxadiazole (3d)

$^1$H NMR (CDCl$_3$) δ ppm: 2.35 (s, 3H), 4.77 (s, 2H), 7.06-7.71 (m, 1H), 7.68-7.72 (m, 1H); MS: m/z=245.1 (M$^+$).

Example 16

5-(Chloromethyl)-3-(4-ethoxyphenyl)-1,2,4-oxadiazole (3e)

$^1$H NMR (CDCl$_3$) δ ppm: 1.43-1.46 (t, 3H, CH$_3$), 4.07-4.12 (q, 2H, OCH$_2$), 4.73 (s, 2H), 6.96-6.99 (m, 2H), 7.99-8.02 (m, 2H); MS: m/z=239.1 (M$^+$).

Example 17

3-(3-Chloro-4-fluorophenyl)-5-(chloromethyl)-1,2,4-oxadiazole (3f)

$^1$H NMR (CDCl$_3$) δ ppm: 4.74 (s, 2H), 6.98-6.20 (m, 1H), 8.00-8.03 (m, 1H), 8.18-8.21 (m, 1H); MS: m/z=247.0 (M$^+$).

Example 18

5-(Chloromethyl)-3-(4-isopropylphenyl)-1,2,4-oxadiazole (3g)

$^1$H NMR (CDCl$_3$) δ ppm: 1.27-129 (d, 6H, 2×CH$_3$), 2.93-3.00 (q, J=6.83 Hz, 1H), 4.74 (s, 2H), 7.33-7.35 (m, 2H), 7.99-8.01 (m, 2H); MS: m/z=237.1 (M$^+$).

Example 19

5-(Chloromethyl)-3-(4-fluoro-3-methylphenyl)-1,2,4-oxadiazole (3h)

$^1$H NMR (CDCl$_3$) δ ppm: 2.34 (s, 3H, CH$_3$), 4.74 (s, 2H), 7.09e7.13 (m, 1H), 7.87e7.95 (m, 2H); MS: m/z=227.3 (M$^+$).

Example 20

5-(Chloromethyl)-3-(4-fluoro-3-methoxyphenyl)-1,2,4-oxadiazole (3I)

$^1$H NMR (CDCl$_3$) δ ppm: 3.97 (s, CH$_3$), 4.74 (s, 2H), 7.16-7.20 (m, 1H), 7.64-7.68 (m, 2H); MS: m/z=243.2 (M$^+$).

Example 21

General Procedure for the Preparation {5-chloro-2-(2-(3-(substitutedphenyl)-1,2,4-oxadiazol-5-yl)ethyl)phenyl}(phenyl)methanones (5a-i)

A mixture of 5-(chloromethyl)-3-(substitutedphenyl)-1,2,4-oxadiazole (3a-i) (50 mmol), 2-hydroxy-5-chloro-benzophenone 4 (50 mmol), dried acetone (150 mL) and ultra-dried potassium carbonate (100 mmol) was heated under reflux for 8 h, cooled to room temperature and filtered. The filtrate was evaporated to dryness and the residue obtained was purified by silica gel flash column chromatography with ethyl acetate:n-hexane (7:3) as eluent (60-20 silica gel). The physicochemical characteristics of the title compounds (5a-i) are given in Table 1.

Example 22

{5-Chloro-2-[(3-(phenyl)-1,2,4-oxadiazol-5-yl)-methoxy]-phenyl}-(phenyl)-methanone (5a)

FT-IR (cm$^{-1}$): 3063 (ArC—H), 1652 (C=O), 1596, 1483, 1448 (C=C), 1243 (C—O—C), 726 (C—Cl); $^1$H NMR (CDCl$_3$) δ ppm: 5.27 (s, 2H, OCH$_2$), 7.05-7.08 (d, J=8.60 Hz, 1H), 7.27-7.58 (m, 8H), 7.81-7.84 (m, 2H), 7.08-8.02 (m, 2H); $^{13}$C NMR (CDCl$_3$): δ62.06, 98.32, 114.90, 125.62, 125.62, 128.01, 128.46, 128.94, 129.79, 131.42, 131.64, 133.51, 136.98, 138.19, 153.67, 167.93, 174.03, 194.08; LC-MS: m/z=391.0 (M$^+$); Anal. calcd for C$_{22}$H$_{13}$N$_2$O$_3$Cl: C, 67.61; H, 3.87; N, 7.17. Found: C, 67.54; H, 3.95; N, 7.03.

Example 23

{5-Chloro-2-[(3-(4-fluorophenyl)-1,2,4-oxadiazol-5-yl)-methoxy]-phenyl}-(phenyl)-methanone (5b)

FT-IR (cm$^{-1}$): 3064 (ArC—H), 1652 (C=O), 1591, 1483, 1449 (C=C), 1263 (C—O—C), 743 (C—Cl); $^1$H NMR (CDCl$_3$) δ ppm: 5.26 (s, 2H, OCH$_2$), 7.05-7.07 (d, J=8.58

Hz, 1H), 7.14-7.20 (m, 2H), 7.42-7.47 (m, 4H), 7.54-7.59 (m, 1H), 7.81-7.83 (d, J=7.2 Hz, 2H), 8.01-8.05 (m, 2H); $^{13}$C NMR (CDCl$_3$): δ 62.02, 114.88, 116.03, 116.26, 122.37, 122.40, 127.94, 128.46, 129.63, 129.72, 129.79, 131.39, 131.63, 133.51, 136.98, 153.69, 163.45, 165.96, 167.64, 173.93, 194.10; LC-MS: m/z=409.0 (M$^+$); Anal. calcd for C$_{22}$H$_{14}$N$_2$O$_3$ClI: C, 64.64; H, 3.45; N, 6.85. Found: C, 64.52; H, 3.56; N, 6.75.

Example 24

{5-Chloro-2-[(3-(4-iodophenyl)-1,2,4-oxadiazol-5-yl)-methoxy]-phenyl}-(phenyl)-methanone FT-IR (cm$^{-1}$): 3063 (ArC—H), 1655 (C=O), 1592, 1475, 1449 (C=C), 1260 (C—O—C), 743 (C—Cl), 522 (C—I); $^1$H NMR (CDCl$_3$) δ ppm: 5.26 (s, 2H, OCH$_2$), 7.04-7.07 (d, J=8.61 Hz, 1H), 7.41-7.47 (m, 4H), 7.54-7.56 (m, 1H), 7.76-7.86 (m, 6H); $^{13}$C NMR (CDCl$_3$): 562.06, 98.32, 114.91, 125.62, 128.01, 128.46, 128.94, 129.79, 131.42, 131.63, 133.51, 136.98, 138.19, 153.67, 167.93, 174.03, 194.08; LC-MS: m/z=517.0 (M$^+$); Anal. calcd for C$_{22}$H$_{14}$N$_2$O$_3$ClI: C, 51.14; H, 2.73; N, 5.42. Found: C, 51.08; H, 2.89; N, 5.32.

Example 25

{5-Chloro-2-[(3-(2,5-difluoro-4-methylphenyl)-1,2,4-oxadiazol-5-yl)-methoxy]-phenyl}-(phenyl)-methanone (5d)

FT-IR (cm$^{-1}$): 3068 (ArC—H), 2924 (C—H), 1654 (C=O), 1593, 1482, 1452 (C=C), 1264 (C—O—C), 747 (C—Cl); $^1$H NMR (CDCl$_3$) δ ppm: 2.34 (s, 3H, CH$_3$), 5.28 (s, 2H, OCH$_2$), 7.03-7.09 (m, 2H), 7.41-7.47 (m, 4H), 7.54-7.63 (m, 2H), 7.80-7.83 (d, J=7.20 Hz, 2H); $^{13}$C NMR (CDCl$_3$): 514.86, 14.88, 61.89, 112.62, 112.71, 112.77, 112.85, 114.77, 116.05, 116.08, 116.32, 116.35, 119.03, 119.09, 119.27, 119.32, 127.96, 128.48, 129.76, 130.60, 130.68, 130.79, 130.88, 131.37, 131.62, 133.54, 136.98, 153.60, 154.98, 155.00, 155.84, 155.87, 157.50, 157.53, 158.25, 158.27, 164.62, 164.64, 164.68, 164.70, 173.58, 194.11; LC-MS: m/z=441.0 (M$^+$); Anal. calcd for C$_{23}$H$_{15}$N$_2$O$_3$ClF$_2$: C, 62.67; H, 3.43; N, 6.35. Found: C, 62.54; H, 3.56; N, 6.21.

Example 26

{5-Chloro-2-[(3-(4-ethoxyphenyl)-1,2,4-oxadiazol-5-yl)-methoxy]-phenyl}-(phenyl)-methanone (5e)

FT-IR (cm$^{-1}$): 3075 (ArC—H), 2973 (C—H), 1658 (C=O), 1592, 1476, 1446 (C=C), 1276 (C—O—C), 741 (C—Cl); $^1$H NMR (CDCl$_3$) δ ppm: 1.43-1.47 (t, 3H, CH$_3$), 4.06-4.13 (q, 2H, OCH$_2$), 5.24 (s, 2H, OCH$_2$), 6.95-6.98 (m, 2H), 7.04-7.07 (d, J=8.49 Hz, 1H), 7.41-7.46 (m, 4H), 7.53-7.56 (m, 1H), 7.80-7.93 (m, 2H), 7.94-7.96 (m, 2H); $^{13}$C NMR (CDCl$_3$): 514.64, 61.92, 63.58, 114.71, 114.75, 118.27, 127.76, 128.37, 129.02, 129.67, 129.71, 131.28, 131.53, 133.40, 136.93, 153.66, 161.49, 168.11, 173.79, 194.11; LCMS: m/z=435.2 (M$^+$); Anal. calcd for C$_{24}$H$_{19}$N$_2$O$_4$Cl: C, 66.29; H, 4.40; N, 6.44. Found: C, 66.13; H, 4.51; N, 6.15.

Example 27

{5-Chloro-2-[(3-(3-chloro-4-fluorophenyl)-1,2,4-oxadiazol-5-yl)-methoxy]-phenyl}-(phenyl)-methanone (5f)

FT-IR (cm$^{-1}$): 3061 (ArC—H), 1661 (C=O), 1595, 1480, 1448 (C=C), 1260 (C—O—C), 742 (C—Cl); $^1$H NMR (CDCl$_3$) δ ppm: 5.26 (s, 2H, OCH$_2$), 7.04-7.07 (d, J=8.70 Hz, 1H), 7.22-7.27 (m, 1H), 7.28-7.47 (m, 4H), 7.55-7.57 (m, 1H), 7.80-7.83 (m, 2H), 7.90-7.95 (m, 1H), 8.08-8.09 (m, 1H); $^{13}$C NMR (CDCl$_3$): δ 62.04, 114.90, 117.18, 117.40, 121.95, 122.13, 123.39, 123.43, 127.48, 127.56, 128.04, 128.47, 129.78, 130.05, 131.42, 131.65, 133.97, 153.62, 158.73, 161.26, 166.80, 174.24, 194.05; LC-MS: m/z=443.0 (M$^+$); Anal. calcd for C$_{22}$H$_{13}$N$_2$O$_3$Cl$_2$F: C, 59.61; H, 2.96; N, 6.32. Found C, 59.39; H, 3.10; N, 6.23.

Example 28

{5-Chloro-2-[(3-(4-isopropylphenyl)-1,2,4-oxadiazol-5-yl)-methoxy]-phenyl}-(phenyl)-methanone (5g)

FT-IR (cm$^{-1}$): 3062 (ArC—H), 2960 (C—H), 1651 (C=O), 1593, 1479, 1449 (C=C), 1261 (C—O—C), 758 (C—Cl); $^1$H NMR (CDCl$_3$) δ ppm: 1.26-1.30 (d, 6H, 2×CH), 2.95-2.97 (q, J=6.84 Mz, 1H), 5.25 (s, 2H, OCH$_2$), 7.04-7.07 (m, 1H), 7.33-7.35 (d, J=8.16 Hz, 2H), 7.41-7.47 (m, 4H), 7.53-7.56 (m, 1H), 7.81-7.84 (m, 2H), 7.94-7.97 (m, 2H); $^{13}$C NMR (CDCl$_3$): δ 23.76, 34.20, 61.96, 114.78, 123.63, 127.04, 127.54, 127.83, 128.45, 129.75, 129.79, 131.32, 131.61, 133.49, 137.00, 152.75, 153.70, 168.42, 173.62, 194.19; LC-MS: m/z=433.2 (M$^+$); Anal. calcd for C$_{25}$H$_{21}$N$_2$O$_3$Cl: C, 69.36; H, 4.89; N, 6.47. Found: C, 69.25; H, 4.95; N, 6.33.

Example 29

{5-Chloro-2-[(3-(4-fluoro-3-methylphenyl)-1,2,4-oxadiazol-5-yl)-methoxy]-phenyl}-(phenyl)-methanone (5h)

FT-IR (cm$^{-1}$): 3050 (ArC—H), 2932 (C—H), 1655 (C=O), 1616, 1483, 1450 (C=C), 1259 (C—O—C), 750 (C—Cl); $^1$H NMR (CDCl$_3$) δ ppm: 2.33 (s, 3H, CH$_3$), 5.25 (s, 2H, OCH$_2$), 7.04-7.13 (m, 2H), 7.41-7.46 (m, 4H), 7.53-7.56 (m, 1H), 7.80-7.89 (m, 4H); $^{13}$C NMR (CDCl$_3$): δ 14.51, 62.01, 114.86, 115.59, 115.82, 121.94, 121.97, 125.76, 125.94, 126.91, 127.00, 127.89, 128.45, 129.77, 130.81, 130.87, 131.34, 131.63, 133.49, 136.99, 153.70, 162.03, 164.53, 167.76, 173.82, 194.10; LC-MS: m/z=423.0 (M$^+$); Anal. calcd for C$_{23}$H$_{16}$N$_2$O$_3$ClF: C, 65.33; H, 3.81; N, 6.63. Found C, 65.21; H, 3.94; N, 6.55.

Example 30

{5-Chloro-2-[(3-(4-fluoro-3-methoxyphenyl)-1,2,4-oxadiazol-5-yl)-methoxy]-phenyl}-(phenyl)-methanone (5i)

FT-IR (cm$^{-1}$): 3075 (ArC—H), 2970 (C—H), 1647 (C=O), 1612, 1495, 1444 (C=C), 1259 (C—O—C), 740 (C—Cl); $^1$H NMR (CDCl$_3$) δ ppm: 3.95 (s, OCH$_3$), 5.25 (s, OCH$_2$), 7.04-7.07 (d, J=8.61 Hz, 1H), 7.13-7.19 (m, 1H), 7.41-7.46 (m, 4H), 7.53-7.64 (m, 3H), 7.79-7.82 (m, 2H); $^{13}$C NMR (CDCl$_3$): δ 56.24, 62.00, 112.13, 112.17, 114.89, 116.34, 116.59, 120.55, 120.65, 122.46, 122.51, 127.86, 128.37, 129.67, 131.33, 131.56, 133.41, 136.92, 147.95, 148.10, 152.66, 153.62, 156.00, 167.65, 167.67, 173.87, 193.98; LC-MS: m/z=439.0 (M$^+$); Anal. Calcd for $C_{23}H_{16}N_2O_4ClF$: C, 62.95; H, 3.67; N, 6.38. Found: C, 62.81; H, 3.76; N, 6.21.

Physicochemical characteristics of {5-chloro-2-(2-(3-(substitutedphenyl)-1,2,4-oxadiazol-5-yl)ethyl)phenyl}(phenyl)methanones (5a-i) are illustrated in Table 1, below.

TABLE 1

| Comp code | R$^1$ | R$^2$ | R$^3$ | Molecular Formula (Molecular Weight) | Yield$^a$ (%) | m.p. (° C.) |
|---|---|---|---|---|---|---|
| 5a | H | H | H | $C_{22}H_{15}N_2O_3Cl$ (390) | 72 | 108-110 |
| 5b | H | F | H | $C_{22}H_{14}N_2O_3ClF$ (408) | 75 | 96-97 |
| 5c | H | I | H | $C_{22}H_{14}N_2O_3ClI$ (516) | 80 | 124-126 |
| 5d | F | CH$_3$ | F | $C_{23}H_{15}N_2O_3ClF_2$ (440) | 68 | 87-89 |
| 5e | H | OC$_2$H$_5$ | H | $C_{24}H_{19}N_2O_4Cl$ (434) | 75 | 80-82 |
| 5f | H | F | Cl | $C_{22}H_{13}N_2O_3Cl_2F$ (442) | 81 | 85-86 |
| 5g | H | CH(CH$_3$)$_2$ | H | $C_{25}H_{21}N_2O_3Cl$ (432) | 76 | 110-112 |
| 5h | H | F | CH$_3$ | $C_{23}H_{16}N_2O_3ClF$ (422) | 85 | 73-74 |
| 5i | H | F | OCH$_3$ | $C_{23}H_{16}N_2O_4ClF$ (438) | 60 | 84-85 |

$^a$All the yields are on isolated basis. Purified by silica gel flash column chromatography with ethyl acetate:n-hexane (7:3).

Example 31

Larvicidal Screening

*Anopheles arabiensis* was used in the study according to the protocol described by WHO (1975) guidelines in an insectary simulating the temperature (27.5° C.), humidity (70%), and lighting (12/12) of a malaria-endemic environment. One mL of test compound (1 mg/mL) was added to 1 mL of acetone and followed by 249 mL of distilled water to obtain a final concentration of 4 μg/mL. Thirty individuals of 3rd instar larvae were introduced into a container. Negative control was set up using the solvent (acetone) and distilled water, and a positive control included Temephos, which is an active emulsified organophosphate larvicidal used by malaria control programs. Larval mortality was examined for each container separately for 24 h and fed specially made cat food that contained less oil/fat content. The percentage of mortality was determined relative to the initial number of larvae exposed.

Statistical Analysis

Differences in larval mortality between treatments were assessed with generalized linear models using a quasi-Poisson link function. *Anopheles arabiensis* mortality was the dependent variable, while fixed effects were test compounds and observation period (24 and 48 h). A p-value<0.05 was considered statistically significant. Throughout the text, the results are presented as the adjusted mean±the standard error.

The results of the larvicidal screening can be observed in Table 2, below.

TABLE 2

Mortality of *Anopheles arabiensis* larvae exposed for 24 and 48 h to a series of (5-chloro-2-(2-(3-(substitutedphenyl)-1,2,4-oxadiazol-5-yl)ethyl)phenyl)(phenyl)methanones (5a-i) (4 μg/mL) that resulted in high overall larval mortality (>75%).

| Compound code | Mortality in % (Mean ± SEM) | |
|---|---|---|
| | 24 h | 48 h |
| 5b | 91.70 ± 1.61 | 94.68 ± 1.90 |
| 5f | 98.21 ± 1.22 | 100.00 ± 2.01 |
| 5h | 83.58 ± 2.01 | 86.09 ± 1.95 |
| 5i | 79.49 ± 1.09 | 84.70 ± 1.88 |

It is to be understood that the methods of making and the {5-chloro-2-(2-(3-(substitutedphenyl)-1,2,4-oxadiazol-5-yl)ethyl)phenyl}(phenyl)methanones derivatives, and the use of compositions containing the same, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of killing larva comprising applying to said larva or to a target site of insect infestation a larvicidal effective amount of a compound having the formula I:

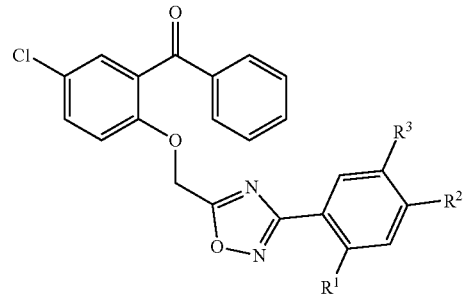

wherein:
R$^1$ is selected from the group consisting of H and F;
R$^2$ is selected from the group consisting of H, F, I, ethoxy, isopropyl, and methyl; and
R$^3$ is selected from the group consisting of H, F, Cl, methyl, and methoxy.

2. The method of killing larva of claim 1, wherein the larva belong to a species *Anopheles arabiensis*.

3. The method of killing larva of claim 2, wherein the overall larva mortality rate is greater than 75% after 24 hours.

4. The method of killing larva of claim 2, wherein the overall larva mortality rate is greater than 80% after 48 hours.

5. The method of killing larva of claim 2, wherein the compound is ingested by the larva.

6. The method of claim 2, wherein the compound is mixed with acetone.

7. The method of killing larva of claim 2, wherein the compound is applied to cat food.

8. A method of killing insects and larva comprising applying to said insects and larva or to a target site of insect infestation a larvicidal effective amount of a larvicidal active compound of the formula I:

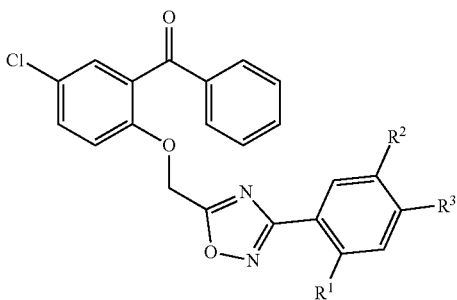

wherein:
$R^1$ is selected from the group consisting of H and F;
$R^2$ is selected from the group consisting of H, F, I ethoxy, isopropyl, and methyl; and
$R^3$ is selected from the group consisting of H, F, Cl, methyl, and methoxy.

9. The compound of claim 8, wherein $R^1$ is H, $R^2$ is selected from the group consisting of H, F, I, ethoxy, isopropyl, and methyl, and $R^3$ is selected from the group consisting of H, Cl, methyl, and methoxy.

10. The compound of claim 8, wherein $R^1$ is F, $R^2$ is methyl, and $R^3$ is F.

11. The method of claim 8, wherein the compound is selected from the group consisting of:
{5-chloro-2-[(3-(phenyl)-1,2,4-oxadiazol-5-yl)-methoxy]-phenyl}-(phenyl)-methanone (5a);
{5-chloro-2-[(3-(4-fluorophenyl)-1,2,4-oxadiazol-5-yl)-methoxy]-phenyl}-(phenyl)-methanone (5b);
{5-chloro-2-[(3-(4-iodophenyl)-1,2,4-oxadiazol-5-yl)-methoxy]-phenyl}-(phenyl)-methanone (5c);
{5-chloro-2-[(3-(2,5-difluoro-4-methylphenyl)-1,2,4-oxadiazol-5-yl)-methoxy]-phenyl}-(phenyl)-methanone (5d);
{5-chloro-2-[(3-(4-ethoxyphenyl)-1,2,4-oxadiazol-5-yl)-methoxy]-phenyl}-(phenyl)-methanone (5e);
{5-chloro-2-[(3-(3-chloro-4-fluorophenyl)-1,2,4-oxadiazol-5-yl)-methoxy]-phenyl}-(phenyl)-methanone (5f);
{5-chloro-2-[(3-(4-isopropylphenyl)-1,2,4-oxadiazol-5-yl)-methoxy]-phenyl}-(phenyl)-methanone (5g);
{5-chloro-2-[(3-(4-fluoro-3-methylphenyl)-1,2,4-oxadiazol-5-yl)-methoxy]-phenyl}-(phenyl)-methanone (5h); and
{5-chloro-2-[(3-(4-fluoro-3-methoxyphenyl)-1,2,4-oxadiazol-5-yl)-methoxy]-phenyl}-(phenyl)-methanone (5i).

12. The method of claim 8, wherein the overall larva mortality rate is greater than 75% after 24 hours.

13. The method of claim 8, wherein the overall larva mortality rate is greater than 80% after 48 hours.

14. The method of claim 8, wherein the compound is mixed with acetone.

15. The method of claim 8, wherein the compound is ingested by a larvae.

16. The method of claim 1, wherein $R^1$ is H, $R^2$ is selected from the group consisting of H, F, I ethoxy, isopropyl, and methyl, and $R^3$ is selected from the group consisting of H, Cl, methyl, and methoxy.

17. The method of claim 1, wherein $R^1$ is F, $R^2$ is a methyl, and $R^3$ is F.

18. The method of claim 1, wherein the compound is selected from the group consisting of:
{5-chloro-2-[(3-(phenyl)-1,2,4-oxadiazol-5-yl)-methoxy]-phenyl}-(phenyl)-methanone (5a);
{5-chloro-2-[(3-(4-fluorophenyl)-1,2,4-oxadiazol-5-yl)-methoxy]-phenyl}-(phenyl)-methanone (5b);
{5-chloro-2-[(3-(4-iodophenyl)-1,2,4-oxadiazol-5-yl)-methoxy]-phenyl}-(phenyl)-methanone (5c);
{5-chloro-2-[(3-(2,5-difluoro-4-methylphenyl)-1,2,4-oxadiazol-5-yl)-methoxy]-phenyl}-(phenyl)-methanone (5d);
{5-chloro-2-[(3-(4-ethoxyphenyl)-1,2,4-oxadiazol-5-yl)-methoxy]-phenyl}-(phenyl)-methanone (5e);
{5-chloro-2-[(3-(3-chloro-4-fluorophenyl)-1,2,4-oxadiazol-5-yl)-methoxy]-phenyl}-(phenyl)-methanone (5f);
{5-chloro-2-[(3-(4-isopropylphenyl)-1,2,4-oxadiazol-5-yl)-methoxy]-phenyl}-(phenyl)-methanone (5g);
{5-chloro-2-[(3-(4-fluoro-3-methylphenyl)-1,2,4-oxadiazol-5-yl)-methoxy]-phenyl}-(phenyl)-methanone (5h); and
{5-chloro-2-[(3-(4-fluoro-3-methoxyphenyl)-1,2,4-oxadiazol-5-yl)-methoxy]-phenyl}-(phenyl)-methanone (5i).

* * * * *